US008585761B2

(12) United States Patent
Theofilos (10) Patent No.: US 8,585,761 B2
(45) Date of Patent: Nov. 19, 2013

(54) EXPANDABLE CAGE WITH LOCKING DEVICE

(75) Inventor: Charles Theofilos, Palm Beach Gardens, FL (US)

(73) Assignee: K2M, Inc., Leesburg, VA (US)

( * ) Notice: Subject to any disclaimer, the term of this patent is extended or adjusted under 35 U.S.C. 154(b) by 243 days.

(21) Appl. No.: 12/602,880

(22) PCT Filed: Mar. 30, 2009

(86) PCT No.: PCT/US2009/038787
§ 371 (c)(1),
(2), (4) Date: Dec. 3, 2009

(87) PCT Pub. No.: WO2009/121059
PCT Pub. Date: Oct. 1, 2009

(65) Prior Publication Data
US 2010/0179656 A1    Jul. 15, 2010

Related U.S. Application Data

(60) Provisional application No. 61/072,176, filed on Mar. 28, 2008, provisional application No. 61/087,046, filed on Aug. 7, 2008.

(51) Int. Cl.
*A61F 2/44* (2006.01)

(52) U.S. Cl.
USPC ....................................... 623/17.11

(58) Field of Classification Search
USPC ...................................... 623/17.11
See application file for complete search history.

(56) References Cited

U.S. PATENT DOCUMENTS

| 4,554,914 | A | 11/1985 | Kapp et al. |
| 5,236,460 | A | 8/1993 | Barber |
| 5,290,312 | A | 3/1994 | Kojimoto et al. |
| 5,336,223 | A | 8/1994 | Rogers |
| 5,360,430 | A | 11/1994 | Lin |
| 5,458,641 | A | 10/1995 | Ramirez Jimenez |

(Continued)

FOREIGN PATENT DOCUMENTS

| SU | 1560184 A1 | 4/1990 |
| WO | WO 2008/005627 A2 | 1/2008 |

OTHER PUBLICATIONS

ISR from Int'l Application No. PCT/US2009/038787 dated May 27, 2009.

(Continued)

*Primary Examiner* — Andrew Yang
*Assistant Examiner* — Olivia C Chang
(74) *Attorney, Agent, or Firm* — Carter, DeLuca, Farrell & Schmidt, LLP (57) ABSTRACT

An apparatus supports the spine between vertebrae and promotes spinal fusion. The apparatus generally includes a first supporting member, a second support member, and an expansion member. The first support member has a first longitudinal passage extending there through and a first supporting end configured to engage tissue. The second supporting member contains a second longitudinal passage extending there through and a second supporting end configured to engage tissue. The second longitudinal passage is dimensioned to receive at least a portion of the first supporting member. The first and second supporting members are configured to move with respect to each other. The expansion member is removably positioned between the first and second supporting members and is adapted to maintain the first and second supporting members in a fixed relative position.

13 Claims, 8 Drawing Sheets

(56) References Cited

U.S. PATENT DOCUMENTS

| | | | |
|---|---|---|---|
| 5,571,190 | A | 11/1996 | Ulrich et al. |
| 5,571,192 | A | 11/1996 | Schönhöffer |
| 5,702,455 | A | 12/1997 | Saggar |
| 5,723,013 | A | 3/1998 | Jeanson et al. |
| 5,776,198 | A | 7/1998 | Rabbe et al. |
| 5,980,522 | A | 11/1999 | Koros et al. |
| 5,989,290 | A | 11/1999 | Biedermann et al. |
| 6,176,881 | B1 | 1/2001 | Schär et al. |
| 6,183,517 | B1 | 2/2001 | Suddaby |
| 6,193,755 | B1 | 2/2001 | Metz-Stavenhagen et al. |
| 6,193,756 | B1 | 2/2001 | Studer et al. |
| 6,200,348 | B1 | 3/2001 | Biedermann et al. |
| 6,241,769 | B1 | 6/2001 | Nicholson et al. |
| 6,296,665 | B1 | 10/2001 | Strnad et al. |
| 6,332,895 | B1 | 12/2001 | Suddaby |
| 6,375,683 | B1 | 4/2002 | Crozet et al. |
| 6,395,034 | B1 | 5/2002 | Suddaby |
| 6,419,705 | B1 | 7/2002 | Erickson |
| 6,500,178 | B2 | 12/2002 | Zucherman et al. |
| 6,524,341 | B2 | 2/2003 | Läng et al. |
| 6,562,074 | B2 | 5/2003 | Gerbec et al. |
| 6,610,090 | B1 | 8/2003 | Böhm et al. |
| 6,616,695 | B1 | 9/2003 | Crozet et al. |
| 6,648,917 | B2 | 11/2003 | Gerbec et al. |
| 6,660,038 | B2 | 12/2003 | Boyer, II et al. |
| 6,730,088 | B2 | 5/2004 | Yeh |
| 6,752,832 | B2 | 6/2004 | Neumann |
| 6,770,096 | B2 | 8/2004 | Bolger et al. |
| 6,830,589 | B2 | 12/2004 | Erickson |
| 6,852,129 | B2 | 2/2005 | Gerbec et al. |
| 6,863,673 | B2 | 3/2005 | Gerbec et al. |
| 6,866,682 | B1 | 3/2005 | An et al. |
| 6,908,485 | B2 | 6/2005 | Crozet et al. |
| 7,025,787 | B2 | 4/2006 | Bryan et al. |
| 7,056,343 | B2 | 6/2006 | Schäfer et al. |
| 7,094,257 | B2 | 8/2006 | Mujwid et al. |
| 7,156,874 | B2 | 1/2007 | Paponneau et al. |
| 7,285,134 | B2 | 10/2007 | Berry et al. |
| 2003/0130739 | A1 | 7/2003 | Gerbec et al. |
| 2003/0181980 | A1 | 9/2003 | Berry et al. |
| 2004/0186569 | A1 | 9/2004 | Berry |
| 2005/0060034 | A1 | 3/2005 | Berry et al. |
| 2005/0209697 | A1 | 9/2005 | Paponneau et al. |
| 2006/0100710 | A1 | 5/2006 | Gutlin et al. |
| 2006/0129244 | A1 | 6/2006 | Ensign |
| 2006/0200244 | A1 | 9/2006 | Assaker |
| 2006/0241762 | A1 | 10/2006 | Kraus |
| 2006/0241770 | A1 * | 10/2006 | Rhoda et al. ............... 623/17.15 |
| 2007/0010887 | A1 | 1/2007 | Williams et al. |
| 2007/0032871 | A1 | 2/2007 | Michelson |
| 2007/0100340 | A1 | 5/2007 | Lange et al. |
| 2007/0250171 | A1 | 10/2007 | Bonin, Jr. |
| 2007/0255408 | A1 | 11/2007 | Castleman et al. |
| 2007/0270968 | A1 | 11/2007 | Baynham et al. |
| 2007/0282441 | A1 | 12/2007 | Stream et al. |

OTHER PUBLICATIONS

ISR from Int'l Application No. PCT/US2009/038780 dated Nov. 13, 2009.

* cited by examiner

FIG. 11

EXPANDABLE CAGE WITH LOCKING DEVICE

CROSS-REFERENCE TO RELATED APPLICATIONS

The present application claims priority to, and the benefit of, U.S. Provisional Patent Application No. 61/072,176, filed on Mar. 28, 2008, and U.S. Provisional Patent Application No. 61/087,046, filed on Aug. 7, 2008, the contents of each of these prior applications are incorporated by reference herein in their entirety.

BACKGROUND

1. Technical Field

The present disclosure relates to apparatus and methods for treating spinal conditions and, more particularly, to an expandable cage with a locking device for supporting adjacent vertebrae.

2. Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as inter-vertebral discs. Inter-vertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the inter-vertebral discs. Corpectomy involves removal of the vertebral body as well as the adjacent inter-vertebral discs.

A number of spinal surgical devices may be used to promote bony fusion after decompressing the spinal nerves. For instance, surgeons often replace the diseased vertebral tissue with one or more spinal cages and bone support matrix. Spinal cages support adjacent vertebral segments, while furthering spinal fusion of adjacent vertebral bodies. Scientists and clinicians have developed a number of devices and methods for decompressing spinal nerves. Improvements to this methods and devices are nevertheless still possible.

SUMMARY

The present disclosure relates to an apparatus for supporting adjacent vertebrae and promoting spinal fusion. The apparatus generally includes a first supporting member, a second support member, and an expansion member. The first support member has a first longitudinal passage extending therethrough and a first supporting end configured to engage tissue. The second supporting member contains a second longitudinal passage extending therethrough and a second supporting end configured to engage tissue. The second longitudinal passage is dimensioned to receive at least a portion of the first supporting member. The first and second supporting members are configured to move with respect to each other. The expansion member is removably positioned between the first and second supporting members and is adapted to maintain the first and second supporting members in a fixed relative position.

In addition to the apparatus, the present disclosure relates to a method for supporting adjacent vertebrae. This method includes the following steps: (1) providing an apparatus including first and second supporting members configured to move relative to each other and an expansion member removably positioned between the first and second supporting members, wherein the second supporting member defines a longitudinal passage adapted to receive at least a portion of the first supporting member; (2) distracting adjacent vertebrae; (3) removing vertebral tissue; (4) inserting the apparatus between adjacent vertebrae; and (5) positioning the expansion member between the first and second supporting members to maintain the relative position of the first and second supporting members.

BRIEF DESCRIPTION OF THE FIGURES

The above and other aspects, features, and advantages of the present disclosure will become more apparent in light of the following detailed description when taken in conjunction with the accompanying drawings in which.

DETAILED DESCRIPTION OF THE EMBODIMENTS

Embodiments of the presently disclosed devices and methods will now be described in detail with reference to the drawings, wherein like reference numerals identify similar or identical elements. In the drawings and in the description that follows, the term "proximal" will refer to the end of a tool or device that is closest to the operator, while the term "distal" will refer to the end of the tool or device that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. As used herein, a "bone support matrix" is a material that facilitates new bone growth between the opposing vertebral bodies. Suitable bone support matrices can be resorbable or nonresorbable and osteoconductive or osteoinductive. Examples of suitable bone support matrices include synthetic materials, bone morphogenic proteins (BMPs), and heterologous, homologous, or autologous bone and derivatives thereof. The bone support matrix may be radiolucent on x-rays.

Figure 1:
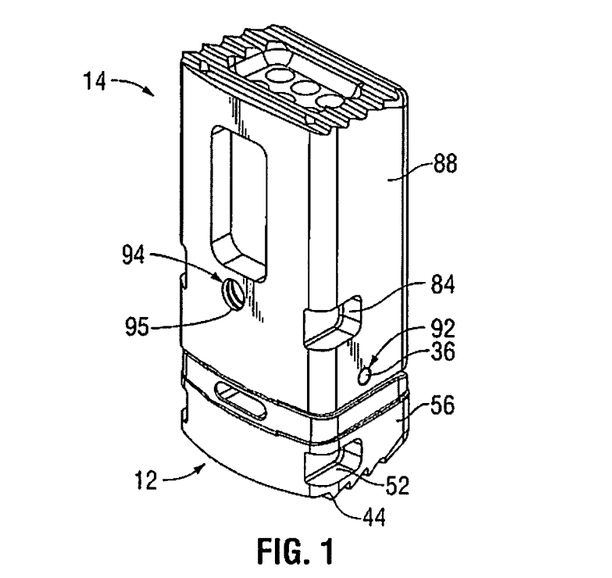
FIG. 1 is a perspective view of an expandable cage according to an embodiment of the present disclosure with an expansion member secured between the first and second supporting members.
Figure 2:
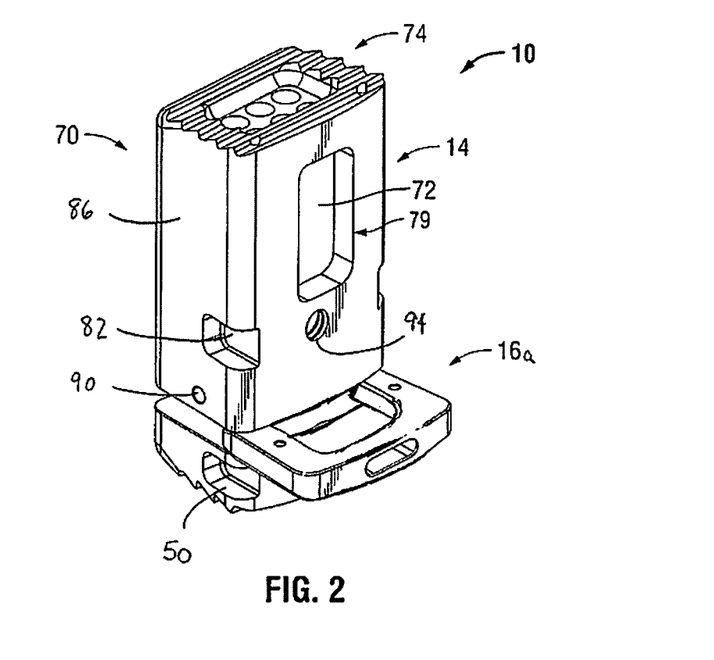
FIG. 2 is a perspective view of the expandable cage of FIG. 1 with the expansion member partially removed from its secured position between the first and second supporting members.
Figure 4A:
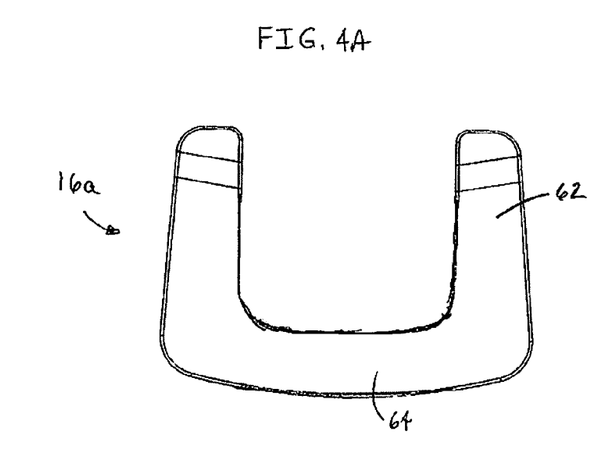
FIGS. 4A-4D are plan views of several embodiments of the expansion member of FIG. 1.
Figure 4B:
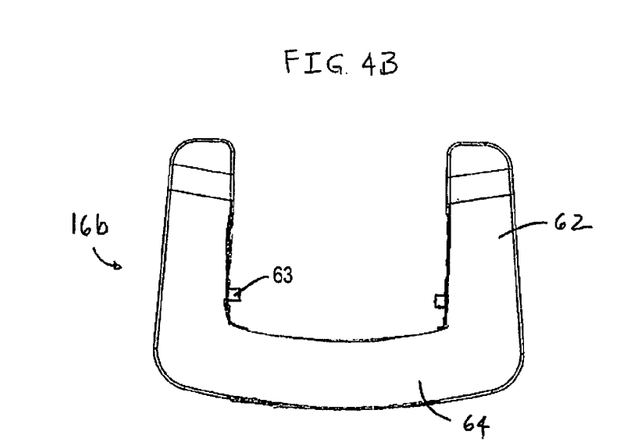
Figure 4C:
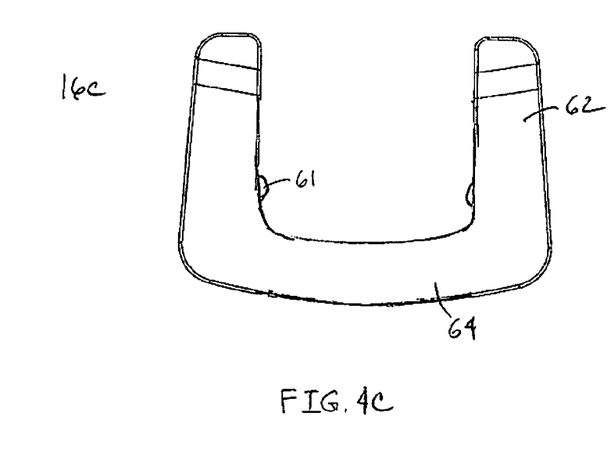
Figure 4D:
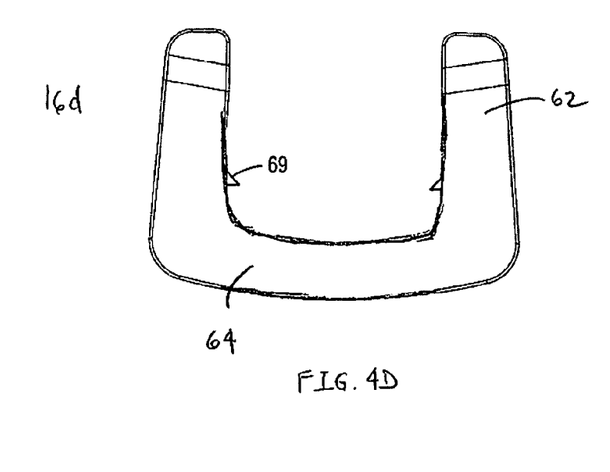

FIGS. 1 and 2 show an expandable cage 10 designed for supporting adjacent vertebra and promoting spinal fusion. Expandable cage 10, which may be made of autologous bone graft, bone allograft, polyetheretherketone (PEEK), titanium, stainless steel, cobalt chrome, polymeric materials, a combination thereof, or any other suitable material, includes first and second supporting members 12, 14 configured to move relative to each other and an expansion member 16a removably positioned between first and second supporting members 12, 14. Other embodiments of the presently disclosed expansion member 16a are illustrated in FIGS. 4B-4D and are discussed in further detail hereinbelow. Expandable cage 10 may be part of a kit including first and second supporting members 12, 14 and several expansion members 16 of different sizes. The different expansion members 16 are dimensioned to maintain first and second supporting members 12, 14 in different relative positions. The plurality of expansion members 16 allows a user to adjust and fix expandable cage 10 at different heights. During operation, the user can adjust the relative position of first and second supporting members 12, 14 to accommodate expandable cage 10 in a variable space located between adjacent vertebrae. After placing expandable cage 10 in such space, the user positions the appropriate expansion member 16 between first and second supporting members 12, 14 to maintain their relative position, thus fixing the expandable cage 10 at the desired height.

Figure 3:
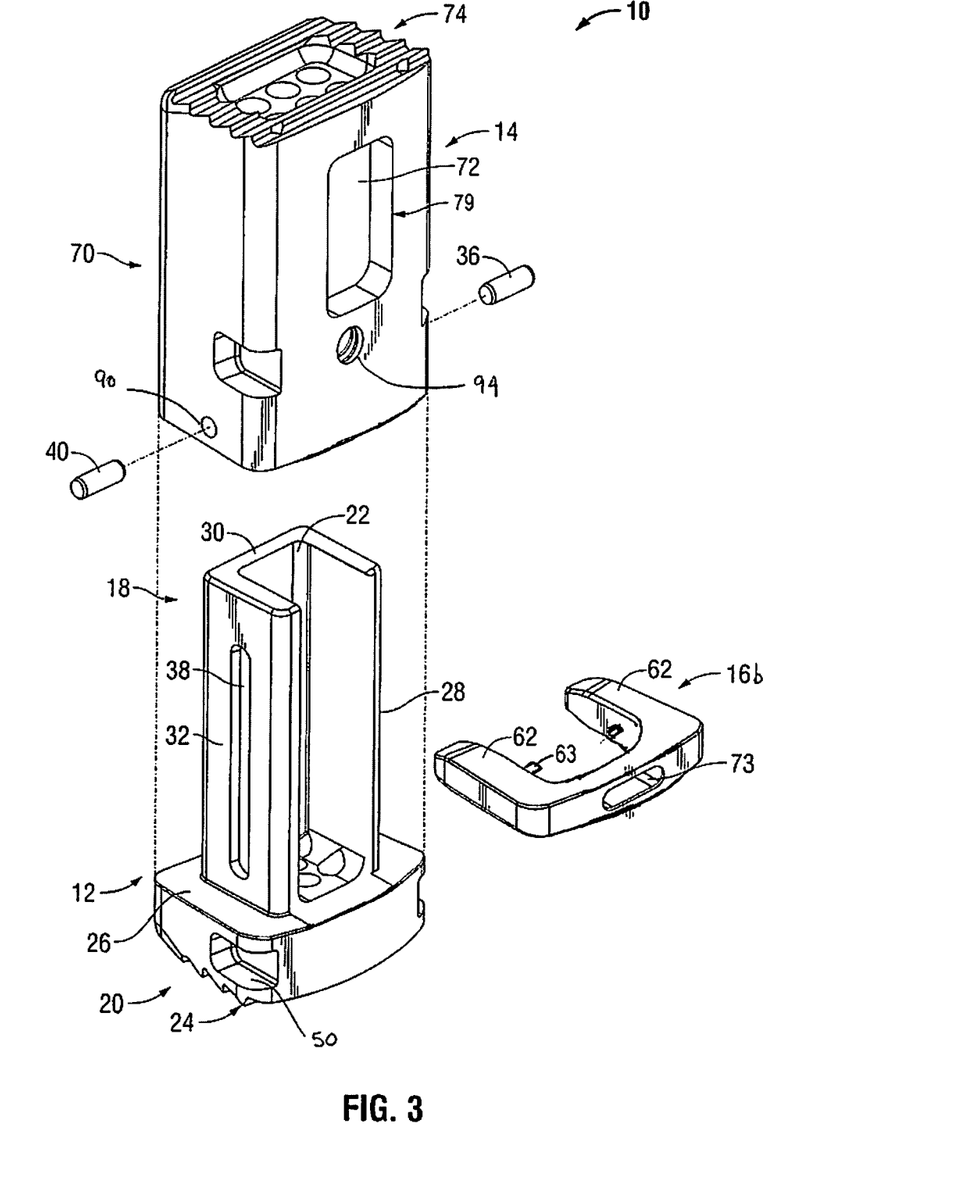
FIG. 3 is perspective exploded view of the expandable cage of FIG. 1.

With reference to FIG. 3, first supporting member 12 of expandable cage 10 includes a first supporting end 20 and an elongate body 18 extending from first supporting end 20. As seen in FIG. 3, elongate body 18 may be a C-shaped structure. It is envisioned, however, that elongate body 18 may have any suitable structure, shape or configuration. Regardless of its shape, elongate body 18 defines a longitudinal passage 22 extending therethrough. Longitudinal passage 22 is adapted to receive optional autologous bone graft, bone allograft, bone slurry, bone chips, bone morphogenic protein or any other bone support matrix suitable for promoting bony union between vertebrae. In the embodiment depicted in FIG. 3, first, second, and third walls 28, 30, 32 collectively define longitudinal passage 22 and form elongate body 18. Each of first, second and third walls 28, 30, 32 have flat outer surfaces. Second wall 30 interconnects first and third walls 28, 32. First wall 28 is transversely secured to second wall 30, while second wall 30 is transversely attached to third wall 32. First and third walls 28, 32 are arranged in parallel with respect to each other. Second wall 30, on the other hand, is arranged in a substantially orthogonal relationship with first and third walls 28, 32.

First wall 28 contains a slot (not shown) disposed along an outer surface thereof. The slot of first wall 28 is substantially identical to that of third wall 32 that is discussed more fully below. The slot of first wall 28 is configured to slidably receive a pin 36. The slot and pin 36 jointly allow first and second supporting members 12, 14 to slide relative to each other while maintaining alignment of the parts, inhibiting relative rotational movement of the parts, and inhibiting separation of the parts. Third wall 32 features a slot 38 formed along an outer surface thereof. Slot 38 is adapted to slidably receive a pin 40. Slot 38 and pin 48 cooperatively allow first and second support members 12, 14 to slide with respect to each other while maintaining alignment of the parts, inhibiting relative rotational movement of the parts, and inhibiting separation of the parts.

Figure 5:
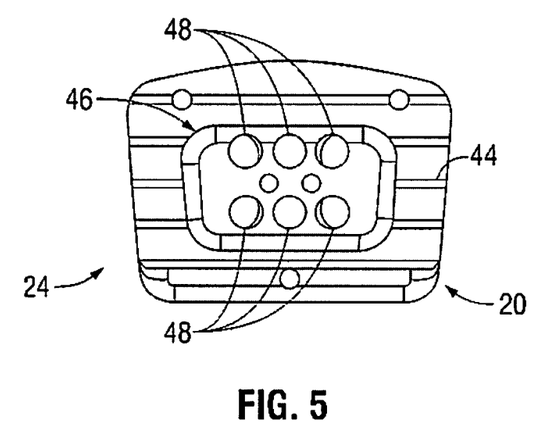
FIG. 5 is a bottom view of the expandable cage of FIG. 1.

With reference to FIGS. 3 and 5, first supporting end 20 includes an engagement surface 24 and an abutting surface 26 disposed in directly opposite relation with respect to each other. Abutting surface 26 faces second supporting member 14, whereas engagement surface 24 faces away from second supporting member 14, when second support member 14 is at least partially placed over first supporting member 12. Engagement surface 24 contains a plurality of teeth 44 adapted to engage a vertebra, or any other kind of tissue, and a recess 46 disposed around a central area thereof. Teeth 44 are arranged in longitudinal rows spreading along the width of engagement surface 24. Each tooth 44 defines an oblique angle in relation to the abutting surface 26. Nonetheless, engagement surface 24 may alternatively have teeth 44 having other configurations and arrangements or any other structure capable of engaging tissue. Recess 46 has a substantially rectangular shape and is configured to receive any suitable bone support matrix to promote spinal fusion between adjacent vertebrae.

As seen in FIG. 5, first supporting member end 20 further includes at least one hole 48 disposed in recess 46. Hole 48 extends through first supporting end 20 and provides access to longitudinal passage 22 (FIG. 3). During use, bone support matrix enters longitudinal passage 22 through hole 48. In the embodiment depicted in FIG. 5, first supporting end 20 includes six (6) holes 48 having circular cross-sections and arranged in longitudinal rows. First supporting end 20, however, may have fewer or more holes 48. Furthermore, holes 48 may have any other suitable configuration or arrangement.

As shown in FIGS. 1 and 2, first supporting end 20 additionally includes cavities 50, 52 disposed on opposite lateral sides 54, 56 thereof. Each cavity 50, 52 is adapted to receive an arm of an insertion tool as is known in the art. During operation, a user may advance expandable cage 10 toward the desired surgical site by positioning the arms of the insertion tool within cavities 50, 52 of first supporting end 20 and advancing the insertion tool toward the surgical site.

Referring again to FIG. 3, first supporting end 20 includes an abutment surface 26, as discussed above. Abutment surface 26 interconnects first, second, and third walls 28, 30, 32 and abuts at least a portion of expansion member 16b when expansion member 16b is placed between first and second supporting members 12, 14. Expansion member 16b includes a pair of legs 62 extending transversely with respect to a backspan 64. With additional reference to FIGS. 4A-4D, several embodiments of the presently disclosed expansion member 16 are shown. In FIG. 4A, expansion member 16a includes a backspan 64 and a pair of legs 62 extending therefrom forming a generally C-shaped configuration. Expansion member 16a may be manufactured in different sizes such that when assembled with the first and second supporting members 12, 14, the expandable cage 10 is adaptable for a number of differently sized spaces between vertebral bodies. Further still, expansion member 16a is maintained in position between support members 12, 14 by the forces applied by the support members 12, 14 when the expandable cage 10 is situated between the vertebral bodies.

Alternatively, as seen in FIG. 4B, the expansion member 16b also includes the backspan with legs 62. Posts 63 are positioned along an inner surface of the legs 62 in an opposing manner. The posts 63 are configured and adapted to fit within the slots of the first and third walls 28, 32 of the first support member 12. The legs 62 flex outwards during insertion of the expansion between the support members 12, 14 and the posts 63 are slidably received in the slots. This arrangement inhibits inadvertent removal of the expansion member 16b and/or minimizes the possibility that the expansion member 16b will become separated from the assembled expandable cage 10 as installed between vertebral bodies. The region where the legs 62 connect to the backspan 64 may have different amounts of resiliency that allows flexing of the legs 62 such that the posts 63 are separated from the slots, thereby allowing a physician to remove the expansion member 16b from the expandable cage 10. Expansion member 16c is substantially similar to expansion member 16b, with the posts 63 being replaced by hemispherical buttons 61. Expansion member 16d differs in that the posts 63 are replaced by teeth 69. In each of these embodiments, the posts 63, buttons 61, and teeth 69 may be made from a frangible material allowing removal without flexing the legs 62. In this instance, the region where the legs 62 connect to the back 64 may have reduced resiliency. Additionally, similar to expansion member 16a, expansion members 16b-16d may be made in various sizes with the attendant advantages discussed hereinabove with respect to expansion member 16a9

Figure 6:
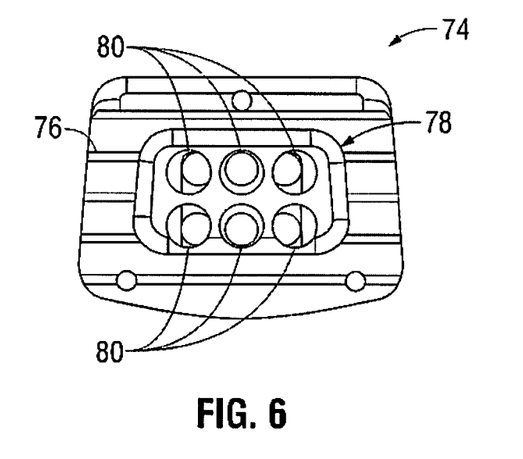
FIG. 6 is a top view of the expandable cage of FIG. 1.

With continued reference to FIG. 3, second supporting member 14 includes an elongate body 70 defining a longitudinal passage 72 and a second supporting end 74. Elongate body 70 additionally includes a rectangular aperture 79 leading to longitudinal passage 72. Longitudinal passage 72 is dimensioned to slidably receive elongate body 18 of first supporting member 12 and is configured to receive bone support matrix. Second supporting end 74 includes a plurality of teeth 76 (FIG. 6) configured to engage tissue. As seen in FIG. 6, teeth 76 are arranged in longitudinal rows spanning the width of second supporting end 74. Each tooth 76 defines an oblique angle relative to the second supporting end 74. Second supporting end 74 further includes a recess 78 (FIG. 6) disposed around a central area thereof. Recess 78 is adapted to receive bone support matrix therein. Additionally, second supporting end 74 includes at least one hole 80 (FIG. 6) located in recess 78. Hole 80 provides access to longitudinal passage 72. In use, bone support matrix migrates from recess 78 to longitudinal passage 72 through hole 80. In the depicted embodiment, second supporting end 74 contains six (6) holes 80 having circular cross-sections and arranged in longitudinal rows (FIG. 6). Second supporting end 74, however, may include more or fewer holes 80 having different configurations and arrangements.

With reference to FIGS. 1 and 2, second supporting member 14 additionally includes cavities 82, 84 positioned on opposite lateral sides 86, 88. Each cavity 82, 84 is adapted to receive the arm of an insertion tool. Second supporting member 14 also has holes 90, 92 on each lateral side 86, 88. Hole 90, which is located on lateral side 86, provides pin 40 access to slot 38, whereas hole 92, which is positioned on lateral side 88, provides pin 36 access to slot 34. Moreover, second supporting member 14 contains an opening 94 (FIG. 1) leading to longitudinal passage 72. Opening 94 includes an inner thread 95 (FIG. 1) and is adapted to receive a pin of the insertion tool. Further, opening 96 is configured to receive another portion of the insertion tool. Opening 94 is positioned on a front surface of second support member 14, as seen in FIG. 1.

Figure 7:
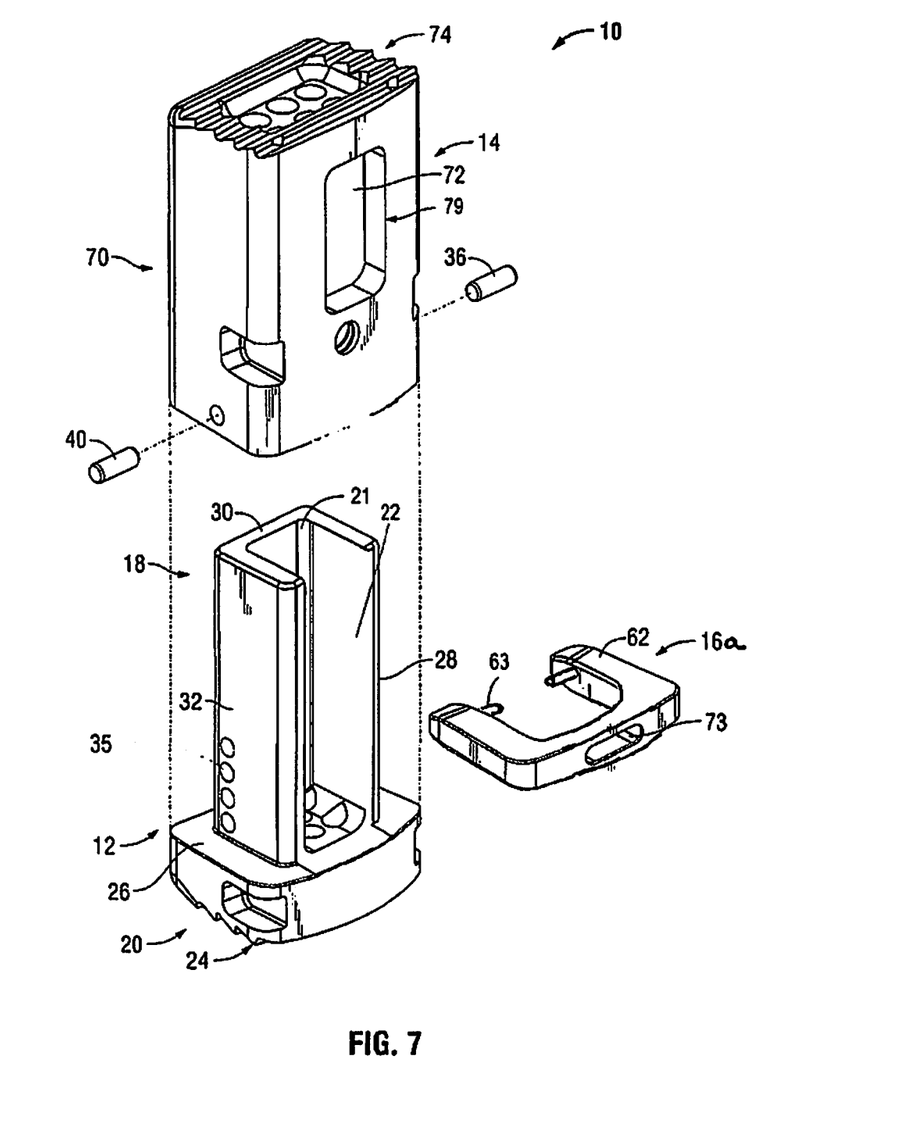
FIG. 7 is a perspective exploded view of an alternate embodiment of the presently disclosed expandable cage.
Figure 8A:
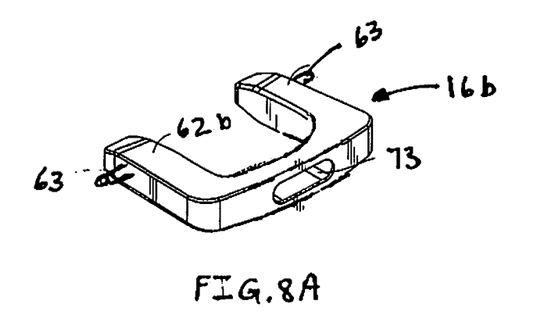
FIGS. 8A-8B are alternate embodiments of the expansion member of FIG. 1.
Figure 8B:
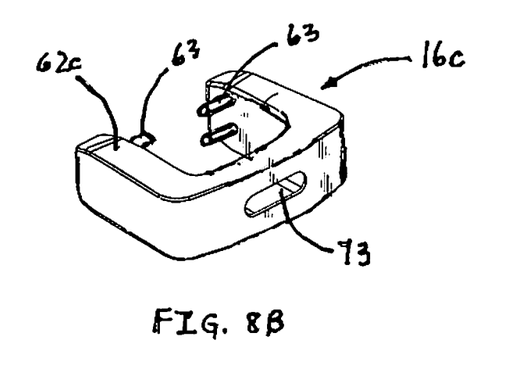

A further embodiment of the expandable cage 10 is shown in FIG. 7. In this embodiment of the expandable cage 10, the slots on the first and third walls 28, 32 are replaced by a plurality of orifices 35 that are vertically oriented along the first and third walls 28, 32. Each orifice 35 is adapted and configured to receive the post 63 of expansion member 16a and provides secure engagement for maintaining the expansion member 16a in position when the expandable cage 10 is assembled. Alternatively, expansion member 16c (FIG. 8B) may be used. Expansion member 16c differs from expansion member 16a in that it includes a number of posts 63 vertically arranged on the inner surfaces of the legs 62c. This arrangement accommodates thicker expansion members 16c, as with the previously disclosed embodiments, the posts 63 may be formed from a frangible material and/or the region connecting the legs 62 and the backspan 64 may be resilient for allowing intentional removal of the expansion member 16c. FIG. 8A illustrates an alternative embodiment of the expansion member with posts 63 on the exterior surfaces of the legs configured to engage corresponding structure on the interior surfaces of the cage (not shown).

Figure 9:
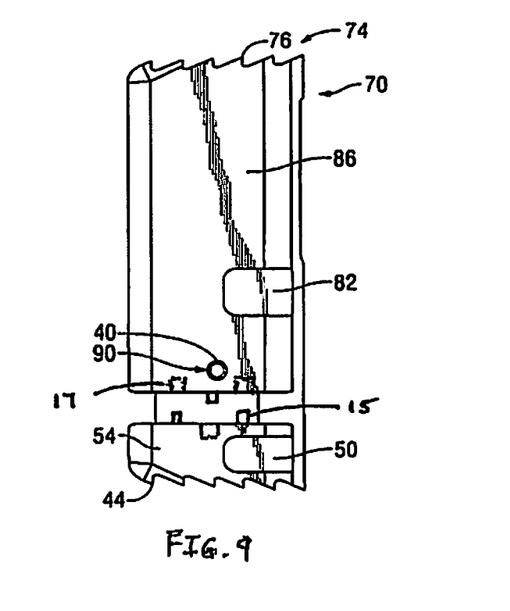
FIG. 9 is a side view of a further embodiment of the presently disclosed expandable cage.
Figure 9A:
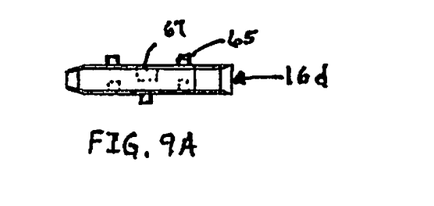
FIG. 9A is a side view of an embodiment of an expansion member for use with the expandable cage of FIG. 9.

In a further embodiment of the expandable cage 10 as shown in FIGS. 9 and 9A, each of the support members 12, 14 include a number of protrusions 15 and a number of recesses 17 (shown in phantom). Expansion member 16d has a corresponding number of protrusions 65 and recesses 67. The protrusions 15, 65 are configured and adapted to be received in the recesses 17, 67. In this embodiment, the expansion member 16d is positioned between the support members 12, 14 and when the support members 12, 14 move towards each other, the protrusions 15, 65 nestle in the recesses 17, 67 thereby ensuring secure engagement and retention of the expansion member 16d in the expandable cage 10. Removal of the expansion member 16d is accomplished by separating the support members 12, 14 or breaking the protrusions 15, 65 in instances where the protrusions 15, 65 are formed from a frangible material.

Figure 10:
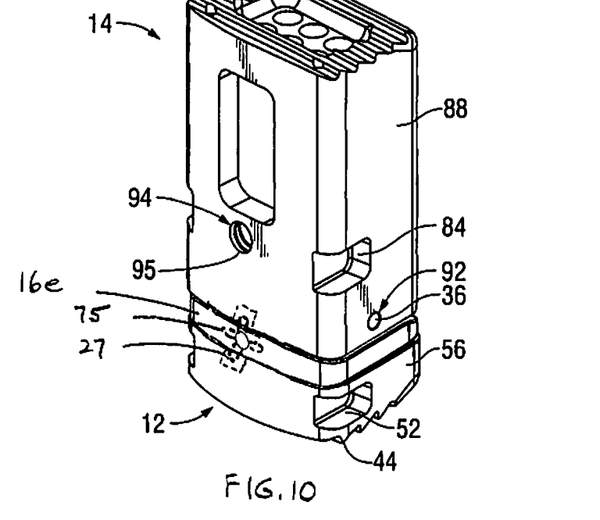
FIG. 10 is a perspective view of an expandable cage according to a further embodiment of the present disclosure.
Figure 11:
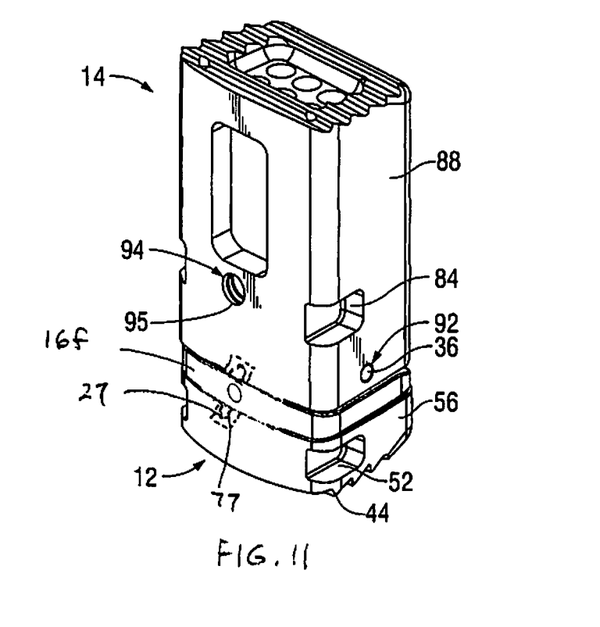
FIG. 11 is a perspective view of an expandable cage according to an alternate embodiment of the present disclosure.

FIGS. 10 and 11 illustrate further embodiments of the expandable cage 10. In these embodiments, the support members 12, 14 include recesses 27. Expansion member 16e (FIG. 10) includes a rotatable screw head operatively coupled to a plurality of wing members 75 (shown in phantom). Similarly, expansion member 16f includes a rotatable screw head operatively coupled to anchor members 77 (shown in phantom). In both versions of the expansion member 16e, 16f, rotation of the screw head expands and retracts the wing members 75 or the anchor members 77. In use, the wing members 75 and the anchor members 77 are retracted within the respective expansion member 16e, 16f and the expansion member 16e, 16f is inserted between the support members 12, 14. Once positioned between the support members 12, 14, the screw head is rotated causing extension of the wing members 75 or the anchor members 77 into the recesses 27, thereby securing the expansion member 16e, 16f between the support members 12, 14. As will be appreciated, rotating the screw head in the opposing direction retracts the wing members 75 or the anchor members 77 from the recesses 27, thereby allowing removal of the expansion member 16e, 16f.

In operation, a user employs an insertion tool to position expandable cage 10 between adjacent vertebrae. Initially, the user holds expandable cage 10 with the insertion tool by placing arms or extensions of the insertion tool within cavities 82, 84. After removing diseased vertebral tissue from the patient, the user advances the insertion tool towards the desired surgical site and places expandable cage 10 in the prepared space between vertebrae. Once expandable cage 10 has been positioned in the desired location, the user moves either first or second support member 12 or 14 relative to the other to adjust the height of expandable cage 10. Once the desired relative position of first and second supporting members 12, 14 has been attained, the user places expansion member 16 between first and second supporting members 12, 14 to fix their relative position. The user is provided with expansion members 16 of different sizes. The user utilizes the expansion member 16 most suitable to achieve the desired expandable cage 10 height. Recesses 46, 78 may be packed with bone support matrix prior to insertion of expandable cage 10, and longitudinal recess 22 may be packed with bone support matrix material after expandable cage 10 has been positioned. Bone support matrix material may be added to expandable cage 10 through aperture 79.

It will be understood that various modifications may be made to the embodiments of the presently disclosed expandable cage and insertion tool. Therefore, the above description should not be construed as limiting, but merely as exemplifications of embodiments. Those skilled in the art will envision other modifications within the scope and spirit of the present disclosure.

What is claimed is:

1. An apparatus for spinal surgery, comprising:
   a first supporting member having a first longitudinal passage extending therethrough, a first supporting end configured to engage tissue;
   a second supporting member having a second longitudinal passage extending therethrough and a second supporting end, the second longitudinal passage being dimensioned to receive at least a portion of the first supporting member, the second supporting end being configured to engage tissue, wherein the first and second supporting members are configured to move with respect to each other; and
   an expansion member removably positionable between the first and second supporting members when at least a portion of the first supporting member is received within the second longitudinal passage of the second support member, the expansion member being configured and adapted to maintain the first and second supporting members in a fixed relationship, the expansion member including a backspan, a pair of legs extending from the backspan, and at least one protrusion configured to engage at least one of the first and second supporting members to maintain the expansion member in position between the first and second supporting members,
   wherein at least one of the first and second supporting members includes a generally C-shaped elongate member with at least one orifice defined in a wall of the elongate member, the at least one orifice configured to receive the at least one protrusion of the expansion member to maintain the expansion member in position between the first and second supporting members.

2. The apparatus of claim 1, wherein at least one of the first and second supporting ends includes a plurality of inclined teeth adapted to engage tissue.

3. The apparatus of claim 1, wherein the first supporting member includes a first elongate body extending from first supporting end, the first elongate body defining the first longitudinal passage.

4. The apparatus of claim 3, wherein the second supporting member includes a second elongate body extending from second supporting end, the second elongate body defining the second longitudinal passage.

5. The apparatus of claim 4, wherein the second longitudinal passage is configured to receive the first elongate body.

6. The apparatus of claim 1, wherein the first supporting end includes at least one hole providing access to the first longitudinal passage.

7. The apparatus of claim 1, wherein the second supporting end includes at least one hole providing access to the second longitudinal passage.

8. The apparatus of claim 1, wherein the at least one of the first and second support members includes a plurality of orifices extending therein and disposed in a vertical orientation.

9. The apparatus of claim 1, wherein at least one of the legs of the expansion member includes the at least one protrusion.

10. A system for spinal surgery, comprising:
    a first supporting member having a first longitudinal passage extending therethrough, a first supporting end configured to engage tissue;
    a second supporting member having a second longitudinal passage extending therethrough and a second supporting end, the second longitudinal passage being dimensioned to receive at least a portion of the first supporting member, the second supporting end being configured to engage tissue, wherein the first and second supporting members are configured to move with respect to each other; and
    one expansion member selected from a set of expansion members, each expansion member removably positionable between the first and second supporting members when at least a portion of the first supporting member is received within the second longitudinal passage of the second supporting member, each expansion member configured and adapted to maintain the first and second supporting members in a fixed relationship and including at least one protrusion configured to engage at least one of the first and second supporting members to maintain each expansion member in position between the first and second supporting members, each expansion member having a height and the height of a first expansion member being different from the height of a second expansion member,
    wherein the second expansion member includes at least one more protrusion than the first expansion member;
    wherein at least one of the first and second supporting members includes a generally C-shaped elongate member with at least one orifice defined in a wall of the elongate member, the at least one orifice configured to receive the at least one protrusion of one of the first and second expansion members to maintain the one of the first and second expansion members in position between the first and second supporting members;
    wherein the second expansion member includes a plurality of protrusions and at least one of the first and second supporting members includes a plurality of orifices extending therein; and
    wherein the protrusions of the second expansion member are received within at least one more orifice than the at least one protrusion of the first expansion member.

11. The system of claim 10, wherein the second height is greater than the first height.

12. The system of claim 10, wherein each of the first and second expansion members includes a backspan and a pair of legs extending from the backspan.

13. The system of claim 12, wherein at least one of the legs of the respective first and second expansion member includes the at least one protrusion of the respective first and second expansion member.

* * * * *